(12) United States Patent
Burns

(10) Patent No.: US 6,544,927 B2
(45) Date of Patent: Apr. 8, 2003

(54) USE OF α2-ADRENERGIC RECEPTOR AGONISTS AND ADRENERGIC INHIBITORS IN REDUCING DEFOLIATION

(75) Inventor: Jacqueline Kay Burns, Auburndale, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/897,830

(22) Filed: Jun. 29, 2001

(65) Prior Publication Data

US 2002/0183205 A1 Dec. 5, 2002

Related U.S. Application Data

(60) Provisional application No. 60/281,194, filed on Apr. 3, 2001.

(51) Int. Cl.$^7$ ............................................... A01N 25/32
(52) U.S. Cl. ....................... 504/104; 504/105; 504/106; 504/108; 504/111; 504/168; 504/171
(58) Field of Search ................................. 504/104, 105, 504/106, 108, 111, 168, 171; 514/772, 975

(56) References Cited

U.S. PATENT DOCUMENTS

| | | | | |
|---|---|---|---|---|
| 4,312,886 A | | 1/1982 | Gluckman | 424/326 |
| 4,746,509 A | * | 5/1988 | Haggiage et al. | 424/449 |
| 5,854,290 A | | 12/1998 | Arnsten et al. | 514/617 |
| 6,147,102 A | | 11/2000 | Borgman | 514/392 |
| 6,352,721 B1 | * | 3/2002 | Faour | 424/473 |

FOREIGN PATENT DOCUMENTS

| | | |
|---|---|---|
| EP | 1147706 | 10/2001 |
| JP | 9169607 | 6/1997 |
| WO | 9911132 | 3/1999 |
| WO | 0042851 | 7/2000 |

OTHER PUBLICATIONS

Moore, *Biochemistry and Physiology of Plant Hormones*, pp. 37–39, Springer–Verlag, New York (1989).
Palmer, et al., "*Effects of Environmental and Nutritional Factors on Production of the Polyketide Phytotoxin Coronatine by Pseudomonas syringae pv Glycinea*", Applied and Environmental Microbiology, vol. 59, pp. 1619–1626 (1993).
Ruffolo, "$_\alpha$–Adrenoceptor Recent Developments", Medical Research Reviews, vol. 14, No. 2, pp. 229–270 (1994).
Zhu, "*Genetic Analysis of Plant Salt Tolerance Using Arabidopsis*", Plant Physiology, vol. 124, pp. 941–948 (2000).
Copy of U.S. Provisional application 60/281,194 filed Apr. 3, 2001.
Bender, et al., "*Pseudomonas syringae Phytotoxins: Mode of Action, Regulation, and Biosynthesis by Peptide and Polyketide Synthetases*", Microbiology and Molecular Biology Review, 63:266–292 (1999).
Ichikawa, et al., "*Identification and role of adenylyl cyclase in auxin signaling in higher plants*", Nature, vol. 390, 698–701, Dec. 1997.
International Search Report for PCT/US02/05352 dated Nov. 11, 2002.
*Oxford Dictionary of Biochemistry and Molecular Biology* (Revised edition) 2000. Oxford University Press, Inc. New York, New York, USA p. 19.

* cited by examiner

Primary Examiner—S. Mark Clardy
(74) Attorney, Agent, or Firm—McDonnell Boehnen Hulbert & Berghoff; Lisa M. W. Hillman

(57) ABSTRACT

The invention provides methods and compositions for reducing defoliation of plants and trees. Preferably, the methods and compositions of the invention reduce defoliation associated with the application of abscission agents or herbicides to plants and trees.

25 Claims, No Drawings

USE OF α2-ADRENERGIC RECEPTOR AGONISTS AND ADRENERGIC INHIBITORS IN REDUCING DEFOLIATION

RELATED APPLICATION

This application claims the benefit of U.S. Provisional Application 60/281,194 filed Apr. 3, 2001, which is herein incorporated in its entirety.

BACKGROUND OF THE INVENTION

Abscission is the ability of plants to slough off organs, such as fruit, by an active separation of cells. Abscission occurs in specific areas of organs to be shed called "abscission zones." Abscission zones contain several layers of starch-filled cells that eventually undergo striking changes such as cell wall digestion that ultimately lead to dropping of the fruit from the stem.

Commercial harvesting of fruit can require deviation from the natural abscission cycle. When harvesting takes place where the abscission layer has not begun to separate, a great deal of force can be required to remove the fruit. The force can damage the fruit or the plant. Presently available abscission agents, such as Ethrel®, can cause unwanted defoliation of a plant or tree. Compositions and methods are needed in the art to reduce the unwanted defoliation of plants and trees, particularly where defoliation is caused by an abscission agent or by an herbicide.

SUMMARY OF THE INVENTION

It is an object of the invention to provide methods and compositions for reducing the defoliation of plants and trees. This and other objects of the invention are provided by one or more of the embodiments described below.

One embodiment of the invention provides a defoliation safener composition. The composition comprises an abscission agent, a thinning agent, or a combination thereof, and an α2-adrenergic receptor agonist, an adrenergic inhibitor, or a combination thereof.

Another embodiment of the invention provides a defoliation safener composition. The composition comprises a plant-compatible surfactant and an α2-adrenergic receptor agonist, an adrenergic inhibitor, or a combination thereof.

Yet another embodiment of the invention provides a defoliation safener composition. The composition comprises a chemical selected from the group consisting of an herbicide, a pesticide, an antimicrobial agent, a fungicide, a fertilizer, and a plant hormone; and an α2-adrenergic receptor agonist, an adrenergic inhibitor, or a combination thereof.

Still another embodiment of the invention provides a method of reducing defoliation of a plant or tree comprising administering an effective amount of an α2-adrenergic receptor agonist, an adrenergic inhibitor, or a combination thereof, to a plant or tree, whereby defoliation is reduced.

Therefore, the invention provides methods and compositions useful in the reduction of defoliation of plants and trees.

DETAILED DESCRIPTION OF THE INVENTION

α2-Adrenergic Receptor Agonists, Adrenergic Inhibitors, and Combinations Thereof Adrenergic receptors (or adrenoceptors) mediate the central and peripheral actions of the primary sympathetic neurotransmitter, norepinephrine, and the primary adrenal medullary hormone, epinephrine. See, Ruffolo et al., *Med. Res. Rev.* 14:229 (1994). Adrenergic receptors mediate a variety of functions and have affinities for many synthetic drugs.

Adrenergic receptors are divided into two subtypes: α1-adrenergic receptors and α2-adrenergic receptors. α2-adrenergic receptors are located on presynaptic nerve terminals, postsynaptically, and in non-synaptic settings, such as human platelets, adipocytes, and vascular smooth muscle. Agonists of α2-adrenergic receptors are useful in treating a variety of diseases including, for example, hypertension, spasticity (resulting from stroke, cerebral trauma, or multiple sclerosis), short stature (in children with constitutional growth delay), glaucoma, gastric ulcers, pain relief, behavior disorders (e.g., attention-deficit hyperactivity disorder, conduct disorder, oppositional defiant disorder, Tourette's syndrome, Lesch-Nyhan syndrome, and the disinhibitory symptoms accompanying post-traumatic stress disorder and dementia), and diarrhea associated with diabetes. See, e.g., U.S. Pat. No. 6,147,102; U.S. Pat. No. 5,854,290; U.S. Pat. No. 4,312,886.

Adrenergic inhibitors are also useful in the invention and include, for example, guanethidine, bethanidine, guanadrel, and debrisoquine.

It has now been discovered for the first time that agonists of α2-adrenergic receptors and adrenergic inhibitors and combinations thereof are useful as safeners, which reduce defoliation of plants and trees. In particular, agonists of α2-adrenergic receptors and adrenergic inhibitors are useful in reducing defoliation of plants and trees resulting from the administration of an abscission agent or herbicide to a plant or tree.

Any α2-adrenergic receptor agonist can be used in the invention. Preferably, the α2-adrenergic receptor agonist is clonidine, UK14,304 (Brimonidine), apraclonidine, guanfacine, guanabenz, phenylephrine, methoxamine, metaraminol, ephedrine, oxymetazoline, naphazoline, tetrahydrozoline, or analogues thereof. An analogue is structurally similar to a particular α2-adrenergic receptor agonist and has similar biological activity to the α2-adrenergic receptor agonist. Similar biological activity means having 5%, 10%, or 15% greater or lesser biological activity than the particular α2-adrenergic receptor agonist.

Furthermore, adrenergic inhibitors can be used in the invention. Preferably, the adrenergic inhibitor is guanethidine (Ismelin), bethanidine, guanadrel (Hylorel), debrisoquine, or analogues thereof.

An analogue is structurally similar to a particular α2-adrenergic receptor agonist or adrenergic inhibitor and has similar biological activity to the α2-adrenergic receptor agonist or adrenergic inhibitor. Similar biological activity means having 5%, 10%, or 15% greater or lesser biological activity than the particular α2-adrenergic receptor agonist or adrenergic inhibitor.

α2-adrenergic receptor agonists and adrenergic inhibitors are known in the art and are commercially available from suppliers such as Sigma/Aldrich (St. Louis, Mo.) and Tocris (Ballwin, Mo.).

Compositions of the invention can be applied to a plant or tree in a mixture with a carrier, or optionally, other auxiliary agents from any one of the standard types of preparations commonly used in agriculture, for example, a dry blend, granules, a wettable powder, an emulsion, and an aqueous solution. Suitable carriers for solid formulations include clay, talc, kaolin, bentonite, terra abla, calcium carbonate, diatomaceous earth, silica, synthetic calcium silicate, kieselguhr, dolomite, powdered magnesia, Fuller's earth, gypsum and the like. Solid compositions can be in the form of dispersible powders or grains, comprising, in addition to an α2-adrenergic receptor agonist or adrenergic inhibitor, a surfactant to facilitate the dispersion of the powder or grains in liquid. Granular compositions can be prepared by, for example, impregnating an α2-adrenergic receptor agonist or adrenergic inhibitor onto or into granulated carriers such as attapulgites or vermiculites, or granulated solid fertilizers.

Liquid forms of the compositions of the invention, which are used for example, for spraying on plants or trees as aerosols or mists, are prepared for application by mixing an α2-adrenergic receptor agonist or adrenergic inhibitor, surfactant, if used, and a liquid carrier, such as water or other liquid to form a stable emulsion or suspension. Liquid compositions of the invention include solutions, dispersions, or emulsions containing an α2-adrenergic receptor agonist or adrenergic inhibitor and optionally, one or more surface-active agents such as wetting agents, dispersing agents, emulsifying agents, or suspending agents.

α2-adrenergic receptor agonist and adrenergic inhibitor compositions of the invention are preferably formulated for use in a mixture with a plant-compatible surfactant, to provide solid or liquid (including a suspension of a solid in a liquid phase) formulations. A plant-compatible surfactant causes little or no damage to plants or trees. Surfactants of the invention can be nonionic, anionic, cationic, or zwitterionic surfactants. A surfactant can be present in a composition of the invention as formulated or, alternatively, a surfactant can be introduced to the compositions of the invention during application to the plant or tree. Preferably, a surfactant is Kinetic® (proprietary blend of poloyalkylene oxide modified polydimethyl siloxane and non-ionic surfactant) (Setre Chemical Co., Memphis, Tenn.), Silwet L-77® (polyalkylene oxide modified heptamethyl trisiloxane) (OSi Specialties, Danbury Conn.), or Tween® 20 (sorbitan mono-9 octadecenoate poly(oxy-1,1-ethanedlyl)) (Sigma-Aldrich, St. Louis Mo.). Preferably, Kinetic® and Silwet L-77® are used at a final concentration of about 1.0 to 0.01%. More preferably, Kinetic® and Silwet L-77® are used at a final concentration of about 0.5 to 0.05 %. Even more preferably, Kinetic® and Silwet L-77® are used at a final concentration of about 0.15%. Preferably, Tween® 20 is used at a final concentration of about 1.0 to 0.01%. More preferably, Tween® 20 is used at a final concentration of about 0.5 to 0.05%. Even more preferably, Tween® 20 is used at a final concentration of about 0.1%.

α2-adrenergic receptor agonist and adrenergic inhibitor compositions of the invention can be used alone or in a mixture or combination with abscission agents, thinning agents, plant hormones, fertilizers, pesticides, herbicides, antimicrobial agents, or fungicides. Preferably, the α2-adrenergic receptor agonist and adrenergic inhibitor compositions of the invention are used in combination or mixture with sulfonylureas and imidazolinones. Even more preferably, the α2-adrenergic receptor agonist and adrenergic inhibitor compositions of the invention are used in combination or mixture with metsulfuron-methyl, an herbicide commonly used to control broadleaf weeds in agronomic crops. Additionally, the α2-adrenergic receptor agonist and adrenergic inhibitor compositions of the invention are especially useful in combination or mixture with an abscission agent such as Ethephon® or Ethrel®.

Compositions of the invention can also be used in plant substantive formulations. Plant substantive formulations mechanically or chemically adhere to a plant and resist removal. Preferred plant substantive agents include various waxes and paraffins, polymers, and sulfur. Wax coated compositions can be prepared by dispersing an α2-adrenergic receptor agonist or adrenergic inhibitor or combinations thereof in molten wax, forming the dispersion into small particles, and cooling the composition below the melting point of the wax. The water resistance of the particles can be controlled by increasing or decreasing the amount of wax employed so as to provide proper release for climatic conditions, i.e., wet areas or dry areas. Additionally, various additives can be dissolved in the wax phase in order to improve the water resistance of the composition or effect other benefits such as slow-release additives or anticaking agents. Other plant substantive agents include casein, salts of alginic acids, cellulose gums and their derivatives, polyvinyl pyrrolidone, vegetable gums, propylene glycol, invert syrup, corn syrup, and the like.

Administration of α2-Adrenergic Receptor Agonists and Adrenergic Inhibitors

α2-adrenergic receptor agonists, adrenergic inhibitors, or combinations thereof are administered to any type of monocotyledon or dicotyledon plant or tree to reduce unwanted defoliation, gummosis, or twig-dieback. A defoliation safener composition of the invention reduces unwanted defoliation, gummosis, or twig-dieback, or a combination thereof. Unwanted defoliation, gummosis, or twig-dieback can be caused by, for example, administration of an abscission agent, a thinning agent, a herbicide, a plant hormone, a fertilizer, a pesticide, an antimicrobial agent, or a fungicide to a plant or tree. Unwanted defoliation, gummosis, or twig-dieback can also occur due to natural causes, including, for example, adverse climatic conditions. The compositions of the invention can be administered to a whole plant or tree or to a portion of a plant or tree. Administration of the compositions of the invention can occur once or can occur two or more times, where each administration is separated by a time interval, such as about 1, 3, 5, or 10 days.

A composition of the invention can be used in combination with an abscission agent or a thinning agent to reduce unwanted defoliation, gummosis, or twig-dieback associated with the agent. Administration of the compositions can occur before, during, or after the application of an abscission or thinning agent. For example, the compositions of the invention can be administered about 1, 3, 5, or 10 days before or after the administration of an abscission or thinning agent. Abscission agents include, for example, Ethrel® (2-chloroethyl phosphonic acid) (Aventis), Ethephon6® (Micro Flo Co., Memphis, Tenn.), Harvade® (Uniroyal Chemical Co., Middlebury, Conn.), FreeFall® (Griffin LLC, Valdosta, Ga.), and Folex® (Aventis). Thinning agents include, for example, naphthanlene acetic acid and Accel® (6-benzyladenine).

In another embodiment of the invention, an α2-adrenergic receptor agonist, adrenergic inhibitor, or combinations thereof are combined with an abscission agent comprising corotanine. Corotanine (COR) is a polyketide that is produced by several pathovars of Pseudomonas syringae. See Bender et al., Microbiol. Mol. Biol. Rev. 63:266–292 (1999). COR is a phytotoxin comprised of coronafacic acid (CFA), a polyketide, and coronamic acid (CMA), an ethylcyclopropyl amino acid. COR does not act as a phytotoxin on trees and plants of the invention, and in particular does not act as a phytotoxin to citrus.

COR is produced by chemical synthesis or by fermentation of cultures of microorganisms that produce COR, either naturally or recombinantly. For example, COR can be produced in vitro by *P. syringae* strain PG4180.N9 or other high coronatine-producing strain. A starter culture is prepared by making 10 mL of broth containing 10 g/L mannitol, 2 g/L L-glutamic acid, 0.5 g/L $KH_2PO_4$, 0.2 g/L NaCl, 0.2 g/L $MgSO_4$, 0.35 g/L yeast extract, and 10 μg/mL kanamycin, pH 7.0. A high coronatine-producing *P. syringae* strain is inoculated into the broth and the starting culture is incubated for 48 hours in an incubator-shaker operating at 200 rpm and 28° C.

A fermentation culture is prepared by making a 1 L broth solution containing 450 mL HSC medium A (1 g/L $NH_4Cl$, 0.2 g/l $MgSO_4$, 4.1 g/L $KH_2PO_4$, 0.3 g/L $KNO_3$, and 10 mL of a solution of 2 mM $FeCl_3$, pH 6.8), 50 mL HSC medium B (20% glucose), and 10 μg/mL kanamycin. 25 mL of a starting culture is added to the fermentation culture and it is incubated for 6 days at 18° C. in an incubator-shaker operating at 200 rpm.

The fermentation culture is centrifuged for 20 minutes at 5,000× g at 4° C. and the pellet is discarded. The pH of the supernatant is adjusted to 2.5 with 1 N HCl. The supernatant containing coronatine is as partitioned three times against ethyl acetate (120 mL ethyl acetate: 100 mL supernatant) and the aqueous phases are discarded. The organic phases are combined and concentrated to 15 mL under vacuum at 35° C. The concentrate is partitioned three times against a solution of 50 mM sodium carbonate, pH 10.5 (15 mL sodium carbonate solution:15 mL concentrate) and the organic phases are discarded. The aqueous phases are combined and the pH is adjusted to 2.5 with 1 N HCl. The aqueous phase is partitioned three times against ethyl acetate (15 mL aqueous:15 mL ethyl acetate). The aqueous phases are discarded and the organic phases are combined. Excess water from the organic phase is removed by adding 5 g anhydrous sodium sulfate and gently agitating. The organic phase is decanted and evaporated to dryness under vacuum at 35° C. The coronatine is resuspended in 20 mL methanol. 0.5 mL of the suspension can be removed for quantitation using HPLC as described in Palmer and Bender (Appl. Environ. Microbiol. 59:1619–1626 (1993)). The remainder of the suspended coronatine can be evaporated to dryness and stored at −80° C., if necessary. Typically, 100 mL of starter culture yields 30 mg of coronatine.

Any fermentation technique, can be used to produce COR, including, for example, batch, fed-batch, semi-batch, or continuous fermentation.

A composition of the invention can also be used in combination with chemicals such as herbicides, plant hormones, fertilizers, pesticides, antimicrobial agents, and fungicides to reduce unwanted defoliation, gummosis, and twig-dieback associated with the administration of the chemicals. Administration of the compositions can occur before, during, or after the application of a chemical.

In one embodiment of the invention, the compositions of the invention along with an abscission agent can be administered to a fruit-bearing plant or tree. The compositions of the invention can be administered in a mixture or combination with an abscission agent or can be administered before or after the administration of an abscission agent. When fruit has reached substantial maturity, a composition of the invention is applied along with an abscission agent, generally about 3 to 20 days prior to harvest, and preferably about 3 to 10 days prior to the harvesting date by administration to the fruit locus or to the whole plant or tree. Optionally, two or more applications of compositions of the invention can be done at different times prior to harvest. Preferably, application is by spray, to run-off.

Preferably, the concentration of an α2-adrenergic receptor agonist, adrenergic inhibitor, or combination thereof is about 25 to 1,000 mg/L (on a weight/volume basis). More preferably, the concentration is about 250 μM (62 mg/L) to 2.0 mM (500 mg/L). Even more preferably, the concentration is about 50 mg/L to 500 mg/L. For citrus trees, approximately 2.5 liters of 250 μM to 2.0 mM is used per fifteen foot tree.

Fruit bearing plants or trees of the invention include the major types of fruit for example, berries such as grapes, blueberries, and oranges; drupes such as peaches, cherries, olives, plums and walnuts; aggregate fruit such as blackberries and raspberries; multiple fruit such as pineapples, figs and mulberries; and accessory fruit such as apples, pears and strawberries. Also included are cotton plants. Preferred fruit of the invention are citrus fruit such as oranges, grapefruit, kumquats, lemons, limes, tangerines, temples, citrange, tangelo, pomelo, and citron.

The following are provided for exemplification purposes only and are not intended to limit the scope of the invention described in broad terms above. All references cited in this disclosure are incorporated herein by reference.

EXAMPLES

Example 1

A solution of an α2-adrenergic agonist was prepared. The solution contained 0.25 to 2 mM of agonist dissolved in water containing an appropriate surfactant. Ethrel® (2-chloroethyl phosphonic acid), an abscission agent, was added at a concentration that causes fruit loosening (in the case of citrus, 100 to 400 mg/L, depending on the variety). The solution was sprayed onto a tree canopy until "run-off," typically about 2.5 liters per 15 foot tree. The solution wet the foliage and fruit, but did not excessively run-off to the ground. Under field conditions the canopies were not sprayed with the agonist-containing solutions if rainfall was anticipated within 24 hours. A positive control, containing a suitable concentration of Ethrel® or other abscission agent, as well as an agonist and surfactant control were sprayed on separate canopies. After several days, usually 3 to 10, differences in leaf drop were measured by counting or weighing dropped leaves. Fruit detachment force (FDF, a measurement defined as the force required to remove fruit from the tree stem) was measured in all treatments.

Table 1 demonstrates the effect of various agonists alone or in combination with 400 ml/L Ethrel® on leaf drop and FDF of calamondin (*Citrus madurensis*). Kinetic® was used as a surfactant. Leaf drop data are leaf loss means of 3 branches times 10 trees, 7 days after application. FDF data are means of 5 fruit times 10 trees, 5 days after application.

TABLE 1

| Treatment | % Cumulative Leaf Drop | % Reduction in FDF |
|---|---|---|
| Clonidine, 1 mM + Ethrel ® | 13.4 | 40.5 |
| Clonidine, 1 mM | 5.8 | 0.5 |
| UK14,304, 0.5 mM + Ethrel ® | 15.6 | 33.4 |
| UK14,304, 0.5 mM | 6.0 | 1.2 |
| Guanabenz, 1 mM + Ethrel ® | 14.1 | 34.6 |
| Gaunabenz, 1 mM | 5.9 | 1.0 |
| Guanafacine, 1 mM + Ethrel ® | 4.8 | 34.8 |
| Guanafacine, 1 mM | 6.5 | 1.0 |
| Kinetic ®, 0.125% | 7.7 | 0 |
| Ethrel ®, 400 mg/L | 68.3 | 41.6 |

Table 2 demonstrates the effect of clonidine alone or in combination with 100 mg/L or 200 mg/L Ethrel® on leaf drop of Valencia orange (*Citrus sinensis*). Kinetic® was used as a surfactant. Data are the leaf loss means of 3 branches times 5 trees, 7 days after application.

TABLE 2

| Treatment | % Cumulative Leaf Drop |
| --- | --- |
| Ethrel ®, 200 mg/L | 43.8 |
| Ethrel ®, 200 mg/L + 2 mM clonidine | 15.1 |
| Ethrel ®, 200 mg/L + 1 mM clonidine | 14.3 |
| Ethrel ®, 100 mg/L | 19.1 |
| Ethrel ®, 100 mg/L + 2 mM clonidine | 7.0 |
| Ethrel ®, 100 mg/L + 1 mM clonidine | 6.1 |
| 2 mM clonidine | 3.2 |
| 1 mM clonidine | 2.7 |
| Kinetic ®, 0.125% | 3.4 |

Example 2

A solution of an α2-adrenergic agonist or adrenergic inhibitor can be prepared that contains about 50 to 500 mg/L of agonist or adrenergic inhibitor, an appropriate surfactant, COR, and water. COR can be added at a concentration that causes fruit loosening, for example, about 100 to about 200 mg/L. The solution can be sprayed onto a tree canopy until "run-off," typically about 2.5 liters per 15 foot tree. The solution should wet the foliage and fruit, but not excessively run-off to the ground. After several days, usually 3 to 10, differences in leaf drop can be measured by counting or weighing dropped leaves. Fruit detachment force can also be measured.

Example 3

The effect of Ethrel, coronatine, coronatine+guanfacine, and adjuvant alone on % cumulative leaf drop in Valencia orange was tested. See Table 3. The data reported in Table 3 are means of 3 branches times 5 trees, 10 days after application.

| Treatment | % Cumulative Leaf Drop |
| --- | --- |
| Ethrel, 200 mg/L | 49.23 |
| coronatine, 200 mg/L | 12.56 |
| coronatine, 200 mg/L + 2 mM guanfacine | 3.07 |
| Kinetic, 0.125% | 2.04 |

I claim:

1. A defoliation safener composition comprising:
   (a) an abscission agent, a thinning agent, or a combination thereof; and
   (b) an α2-adrenergic receptor agonist, an adrenergic inhibitor, or a combination thereof.

2. The composition of claim 1, wherein the α2-adrenergic receptor agonist is selected from the group consisting of clonidine, guanfacine, brimonidine, and guanabenz.

3. The composition of claim 1, wherein the concentration of the α2-adrenergic receptor agonist is about 25 to 1,000 mg/L.

4. The composition of claim 1, wherein the concentration of the α2-adrenergic receptor agonist is about 50 to 500 mg/L.

5. The composition of claim 1, wherein the thinning agent is naphthalene acetic acid or 6-benzyladenine.

6. The composition of claim 1, wherein the adrenergic inhibitor is selected from the group consisting of guanethidine, bethanidine, guanadrel, and debrisoquine.

7. The composition of claim 1, wherein the concentration of the adrenergic inhibitor is about 25 to 1,000 mg/L.

8. The composition of claim 1, wherein the concentration of the adrenergic inhibitor is about 50 to 500 mg/L.

9. The composition of claim 1, wherein the abscission agent is 2-chloroethyl phosphonic acid.

10. The composition of claim 1, wherein the abscission agent is coronatine.

11. A defoliation safener composition comprising:
    (a) a chemical selected from the group consisting of an herbicide, a pesticide, an antimicrobial agent, a fungicide, a fertilizer, and a plant hormone; and
    (b) an α2-adrenergic receptor agonist, an adrenergic inhibitor, or a combination thereof.

12. The composition of claim 11, wherein the α2-adrenergic receptor agonist is selected from the group consisting of clonidine, guanfacine, brimonidine, and guanabenz.

13. The composition of claim 11, wherein the concentration of the α2-adrenergic receptor agonist is about 25 to 1,000 mg/L.

14. The composition of claim 11, wherein the concentration of the α2-adrenergic receptor agonist is about 50 to 500 mg/L.

15. The composition of claim 11, wherein the concentration of the adrenergic inhibitor is about 25 to 1,000 mg/L.

16. The composition of claim 11, wherein the concentration of the adrenergic inhibitor is about 50 to 500 mg/L.

17. A method of reducing defoliation of a plant or tree comprising administering an effective amount of an α2-adrenergic receptor agonist, an adrenergic inhibitor, or a combination thereof, to a plant or tree, whereby defoliation is reduced.

18. The method of claim 17, wherein the an α2-adrenergic receptor agonist is selected from the group consisting of clonidine, guanfacine, brimonidine, and guanabenz.

19. The method of claim 17, wherein the defoliation is the result of a causative agent selected from the group consisting of an abscission agent, a thinning agent, an herbicide, a pesticide, an antimicrobial agent, a fungicide, a fertilizer, and a plant hormone.

20. The method of claim 19, wherein the α2-adrenergic receptor agonist, adrenergic inhibitor, or combination thereof is administered simultaneously with a causative agent.

21. The method of claim 19, wherein the α2-adrenergic receptor agonist, adrenergic inhibitor, or combination thereof, is administered before or after the causative agent.

22. The method of claim 17, wherein the adrenergic inhibitor is selected from the group consisting of guanethidine, bethanidine, guanadrel, and debrisoquine.

23. The method of claim 17, wherein the tree is citrus.

24. The method of claim 23, wherein the citrus is orange.

25. The method of claim 17, wherein the tree is apple or cherry.

* * * * *